(12) United States Patent
Painchaud et al.

(10) Patent No.: US 6,590,665 B2
(45) Date of Patent: Jul. 8, 2003

(54) OPTICAL SENSING DEVICES

(75) Inventors: Yves Painchaud, Sillery (CA); Marc Lévesque, Saint-Augustin-de-Desmaures (CA); Serge Caron, Saint-Augustin-de-Desmaures (CA); Pierre Galarneau, Cap Rouge (CA)

(73) Assignee: Institut National d'Optique, Quebec (CA)

( * ) Notice: Subject to any disclaimer, the term of this patent is extended or adjusted under 35 U.S.C. 154(b) by 0 days.

(21) Appl. No.: 09/810,765

(22) Filed: Mar. 16, 2001

(65) Prior Publication Data

US 2001/0048072 A1 Dec. 6, 2001

(30) Foreign Application Priority Data

Mar. 17, 2000 (CA) .............................................. 2301247

(51) Int. Cl.⁷ .................................................. G01B 9/02
(52) U.S. Cl. ................... 356/480; 356/477; 250/227.14
(58) Field of Search ................................ 356/480, 477, 356/478; 250/227.14

(56) References Cited

U.S. PATENT DOCUMENTS

| | | | | |
|---|---|---|---|---|
| 5,513,913 A | * | 5/1996 | Ball et al. ................... | 374/120 |
| 5,641,956 A | * | 6/1997 | Vengsarkar et al. ... | 250/227.14 |
| 5,909,273 A | * | 6/1999 | Malvern .................... | 356/35.5 |
| 6,277,330 B1 | * | 8/2001 | Liu et al. ................. | 422/82.05 |
| 6,278,810 B1 | * | 8/2001 | Sirkis et al. .................. | 385/12 |

\* cited by examiner

Primary Examiner—Robert H. Kim
Assistant Examiner—Irakli Kiknadze
(74) Attorney, Agent, or Firm—Merchant & Gould P.C.

(57) ABSTRACT

An optical sensor is provided. The sensor includes an optical fiber having a free extremity on which a polymer layer is deposited normal to the longitudinal axis. A light source injects a analytical light beam in the fiber, which is reflected by the polymer layer. The reflected beam is analyzed by a spectrum analyzer, which determines the thickness of the polymer layer based on the Fabry-Perot effect. This thickness is related to a substance to be detected. An optical nose made from a plurality of such sensors is also provided, and may be used to detected a variety of substances.

7 Claims, 2 Drawing Sheets

OPTICAL SENSING DEVICES

FIELD OF THE INVENTION

The present invention relates to optical devices for sensing substances in a solution, and more particularly concerns an optical sensor, an optical nose and a method of making the latter.

BACKGROUND OF THE INVENTION

"Smell-detectors" or "electronic noses" are substance detecting devices based on a technique in full expansion which uses the absorption by polymeric membranes of analytes present in fluids. The absorption of the analytes by the polymeric membranes generates an alteration of its physical properties, such as density, thickness, refractive index, resistivity, etc.

Electronic techniques for measuring these alterations of the properties of the membrane are well documented. For example, the product named "Cyranose 320" (trademark) from the company Cyrano Sciences Inc. is based on such a technique. Typically, an electronic nose is composed of many sensors made from different polymers, each having its own reaction to the presence of a given substance. Electronic noses generally measure the change in resistivity of the polymer membranes. However, since polymers are rarely conductive, it is usually necessary to mix conductive particles, for example carbon-black, to the polymeric material, thereby increasing the conductivity of the membrane. Another major drawback experienced by these devices is sensor drift, which creates the necessity for frequent calibration or "retraining" of the sensors.

Optical based detecting techniques are also known in the art. In these cases, the luminescence of the polymeric membrane when exposed to a given analyte is measured and characterized. The following references study the various aspects of this technique: "Randomly Ordered Addressable High-Density Optical Sensor Arrays" Michael, K. L., Taylor, L. C. Schultz, S. L., Walt, D. R., Anal. Chem. 1998, 70, 1242–1248, "The Use of Optcal-Imagining Fibers for the Fabrication of Array Sensors" Michael, K. L., Ferguson, J. A., Healy, B. G., Panova, A. A., Pantano, P., Walt, D. R., American Chemical Society, 1998; 273–288; "Ordered Nanowell Arrays" Pantano, P., Waft, D. R., Chem. Mater. 1996, 8, 2832–2835; "Combined imaging and chemical sensing of fertilization-induced acid release from single sea urchin eggs", Michael, K. L., Walt, D. R., Anal. Biochem., 1999, 273, 168–178; "Convergent, Self-Encoded Bead Sensor Arrays in the Design of an Artificial Nose" Dickinson, T. A., Michael, K. L., Kauer, J. S., Walt, D. R., Anal. Chem., 1999, 71, 2192–2198; "identification of Multiple Analytes Using an Optical Sensor Array and Pattern Recognition Neural Networks" Johnson, S. R., Sutter, J. M., Engelhardt, H. L., Jurs. P. C., White, J, Kauer, J. S., Dickinson, T. A., Walt, D. R., Anal. Chem, 1997, 69, 4641–4648; "A Chemical-Detecting System based on a cross-reactive optical sensor array", Dickinson, T. A., White, J., Kauer, J. S., Walt, D. R., Nature, 1996, 382, 697–700; and "High-Speed Fluorescence Detection of Explosives Vapor". Albert, K. J., Myrick, M. L., Brown, S. B., Milanovich, F. P., Walt, D. R., SPIE, 1999, 3710, 308–314.

OBJECTS AND SUMMARY OF THE INVENTION

An object of the present invention is to provide a sensing device measuring the change in thickness of the polymer membrane by optical means.

Another object of the invention is to provide such a sensing device for either detecting a particular substance or identifying at least one substance in a solution.

Yet another object of the present invention is to provide a method for making such a device.

Accordingly, the present invention provides an optical sensor for detecting a substance in a solution, comprising:
  an optical fiber having a free extremity;
  a polymer layer deposited on said free extremity of the optical fiber, said polymer layer laying in a plane normal to a longitudinal axis of the optical fiber, the polymer layer having a thickness related to said substance when exposed thereto;
  a light source coupled to the optical fiber for injecting an analytical light beam therein so that said analytical light beam is reflected by the polymer layer to define a reflected light beam; and
  a spectrum analyzer coupled to the optical fiber for receiving the reflected light beam and analyzing said reflected light beam to deduce therefrom the thickness of the polymer layer.

In accordance with another object of the invention, there is provided an optical nose for identifying at least one substance in a solution, said optical nose comprising:
  a plurality of optical sensors, each comprising an optical fiber having a free extremity and a polymer layer deposited on said free extremity, said polymer layer laying in a plane normal to a longitudinal axis of the optical fiber, at least two of said polymer layers being of different types, each polymer layer having a thickness related to said at least one substance when exposed thereto;
  a light source, coupled to the optical fiber of each of the optical sensors, for injecting an analytical light beam therein so that said analytical light beam is reflected by the corresponding polymer layer to define a reflected light beam; and
  a spectrum analyzer coupled to the optical fiber of each of the optical sensors, for receiving each of the reflected light beams, analyzing each of said reflected light beams to deduce therefrom the thickness of the corresponding polymer layer, and identifying the at least one substance corresponding to said thicknesses.

Also, the present invention provides a method of making an optical nose for identifying at least one substance in a solution, the method comprising the steps of:
  a) providing a plurality of optical fibers, each having a free extremity;
  b) depositing a polymer layer on the free extremity of each optical fiber in a plane normal to a longitudinal axis of the optical fiber, at least two of said polymer layers being of different types, each polymer layer having a thickness related to the at least one substance when exposed thereto;
  c) coupling each of the optical fibers to a light source for injecting an analytical light beam therein, so that said analytical light beam is reflected by the corresponding polymer layer to define a reflected light beam;
  d) coupling each of the optical fibers to a spectrum analyzer for receiving each of the reflected light beams and for analyzing each of said reflected light beams to deduce therefrom the thickness of the corresponding polymer layer; and
  e) exposing-the optical nose to solutions including known substances and identifying the thicknesses of the polymer layers corresponding to said known substances.

DESCRIPTION OF PREFERRED EMBODIMENTS OF THEE INVENTION

Figure 1:
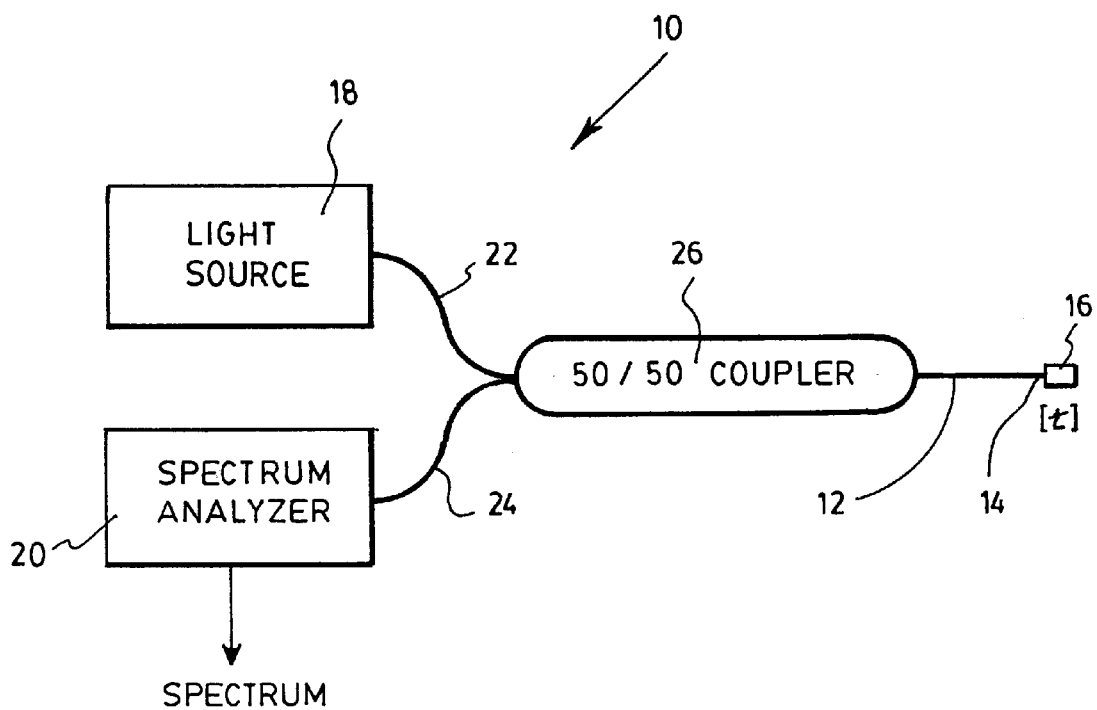
FIG. 1 is a schematic representation of an optical sensor according to an embodiment of the present invention.

With reference to FIG. 1, there is shown an optical sensor 10 for detecting a substance in a solution in accordance with a first preferred embodiment of the invention.

The sensor 10 first includes an optical fiber 12, which could be a typical silica fiber or be made of any other appropriate material. The fiber 12 has a free extremity 14, which has been cut along the cross section of the fiber 12 so as to define a plane normal to its longitudinal axis. A polymer layer 16 is deposited on the free extremity 14, and extends in this normal plane. The polymer layer 16 has a thickness t related to substance to be detected when exposed thereto, as will be further explained below. Any number of polymeric materials may be used depending on the desired-sensibility of the device. The same polymers as those used for electronic noses may equally be chosen for the present invention. Example of such polymers include polydimethylsiloxane (PDMS), polyoctylmethylsiloxane (POMS), poly(isopropylcarboxylic acid)methylsiloxane (PiPCAM S), poly(cyanopropyl)methylsiloxane (PCPMS), poly(aminopropyl)methylsiloxane (PAPMS), poly(cyanopropyl)methylsiloxane (PCPMS), (etc.)

A light source 18 is coupled to the optical fiber 12. The light source preferably emits an analytical light beam which is preferably a broadband signal, such as white light. A scanning in wavelength of the analytical light beam may also be considered. The analytical light beam is injected into the optical fiber 12, wherein in propagates toward the polymer layer 16 where it is reflected at least partially. A reflected light beam is therefore generated in counter propagation in the fiber 12. The reflected light beam is analyzed by a spectrum analyzer 20, which is coupled to the optical fiber 12 for this purpose.

Preferably, a source fiber 22 is provided for conveying the analytical light beam from the light source 18 to the optical fiber 12, and an analyzer fiber 24 conveys the reflected light beam from the optical fiber 12 to the spectrum analyzer 20. A 50/50 coupler 26 is preferably provided for coupling the source fiber 22 and analyzer fiber 24 to the optical fiber 12. In this manner, an optical beam incident on the coupler 26 is divided into two equal beams each transmitted in one of the other two branches connected to the coupler 26. This setup of course generates a decrease in the useful signal intensity, and other coupling schemes may of course be devised in accordance with the general knowledge of, those skilled in the art without departing from the scope of the present invention.

In use, the above described sensor operates as follows. The free extremity 14 of the fiber 12 is inserted in the solution containing the substance to be detected. The particular polymer material of the layer 14 has been chosen to have a particular reaction to this given substance, that is that its thickness will increase to a known value when in its presence. The objective of the operation is therefore to measure this thickness. The analytical light beam is injected into the fiber 12, and is partially reflected when it encounters the refractive index change at the polymer layers boundaries. Two such boundaries are present, a first one between the optical fiber 12 and the polymer layer 16, and a second one between the polymer layer 16 and the solution media. Partial reflection occurring at both boundaries, a periodic variation will be introduced in the reflected light beam, in accordance with the Fabry-Perot effect. This shift is directly related to the thickness of the polymer layer. Using interferometric, refractive or diffractive analyzing techniques well known of those in the art, the thickness of the polymeric layer may be deduced by the analyzer 20 from the spectrum of the reflected light beam.

Figures 2, 2A:
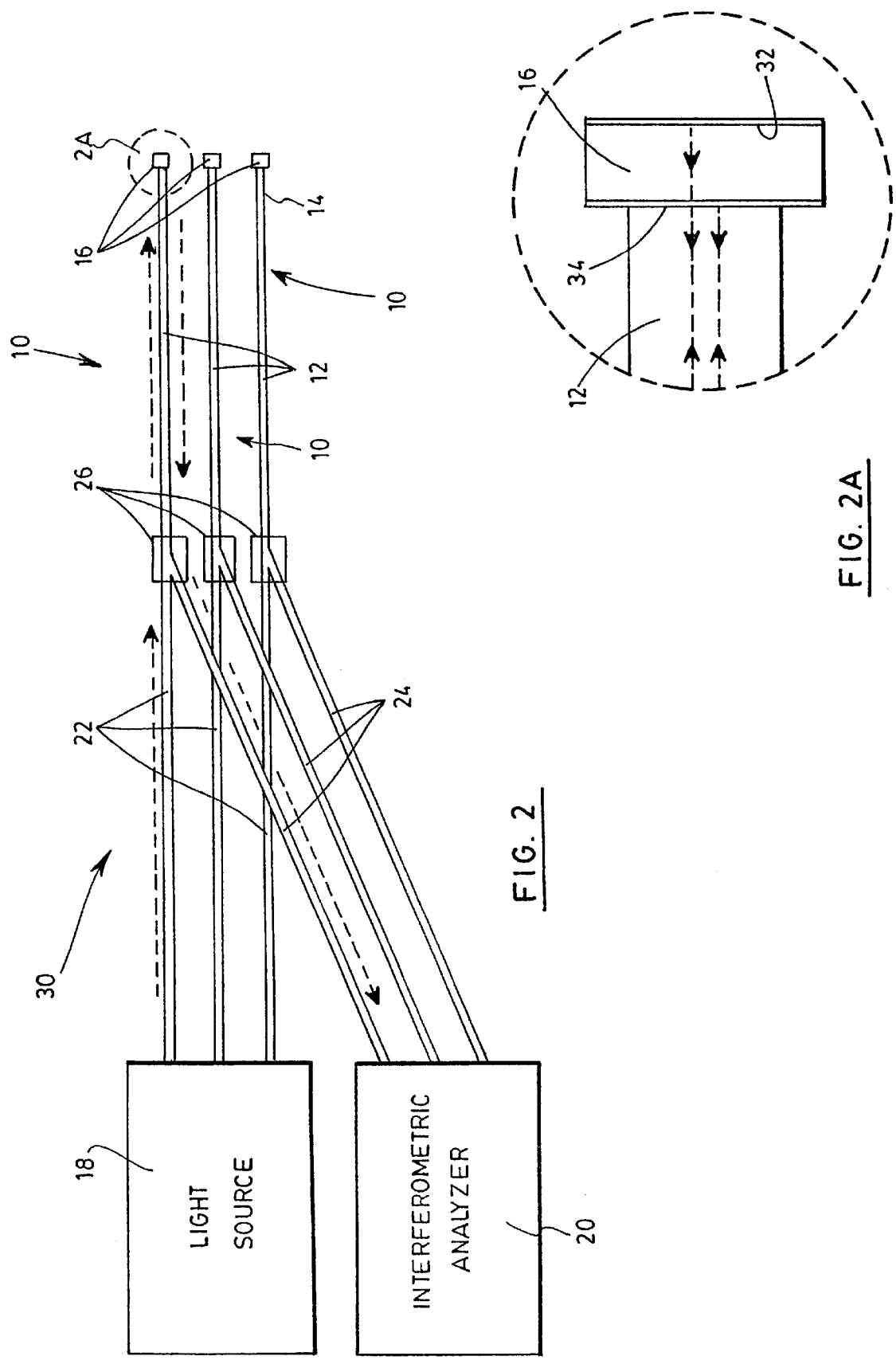
FIG. 2 is a schematic representation of an optical nose according to another embodiment of the present invention.
FIG. 2A is an enlarged view of section 2A of FIG. 2.

With reference to FIG. 2 there is shown an optical nose 30 for identifying at least one substance in a solution in accordance with a second preferred embodiment of the invention.

A plurality of optical sensors 10 similar to those described above are provided, each comprising an optical fiber 12 having a free extremity 14 and a polymer layer 16 deposited on this free extremity. At least two of the materials used to form the polymer layers 16 are of different types. Preferably, the nose 30 includes a many optical sensor 10 each having a different polymer layer 16. The thickness t of each polymer layer 16 is related to the least one substance when exposed thereto.

The optical nose 30 preferably includes a single light source 18 which may be embodied as described above. The source 18 is coupled to the optical fiber 12 of each of the optical sensors preferably through source fibers 22. Alternatively, a single signal may be produced by the source 18, and subsequently split to feed each sensor 10. As before, an analytical light beam is injected in each of the sensors 10, and is reflected by the corresponding polymer layer 16 to define a reflected light beam.

As with the light source 18, a single spectrum analyzer 20 is provided and is preferably coupled to the optical fiber 12 of each of the optical sensors 10 through analyzer fibers 24. The analyzer 20 receives each of the reflected light beams, analyzes each of them to deduce therefrom the thickness of the corresponding polymer layer, and compares this data to predetermined values identifying the substance or substances to which it corresponds.

In a preferred embodiment, the spectrum analyzer may include a neural network adapted to identify a plurality of substances based on the corresponding thicknesses of the polymer layers. Such networks are presently considered for electronic noses, and vary in complexity depending on the range of the desired analytical power.

Referring to FIG. 2A, there is shown another preferred characteristic of the invention, which although illustrated with respect to the embodiment of FIG. 2 may also be included in the one of FIG. 1. In accordance with this feature, a reflective optical coating 32 may be deposited over the polymer layer 16 of a given sensor. This optical coating is preferably a thin film of any appropriate material, metallic or otherwise, and is provided to increase the reflective properties of the polymer layer/solution boundary and thereby increase the strength of the reflected beam. Similarly, an appropriate semi-reflective optical coating 34 may be provided between the free extremity of the optical fiber 12 and the polymer layer 16.

In accordance with another aspect of the present invention, method of making an optical nose, such as the one described above, is preferably provided. The method includes the following steps:

a) providing a plurality of optical fibers, each having a free extremity.

b) depositing a polymer layer on the free extremity of each optical fiber in a plane normal to a longitudinal axis of the optical fiber, at least two of the polymer layers being of different types. Each polymer layer has a thickness related to the at least one substance when exposed thereto.

c) coupling each of the optical fibers to a light source for injecting an analytical light beam therein, so that said analytical light beam is reflected by the corresponding polymer layer to define a reflected light beam.

d) coupling each of the optical fibers to a spectrum analyzer for receiving each of the reflected light beams, and for analyzing each of the reflected light beams to deduce therefrom the thickness of the corresponding polymer layer.

and e) exposing the optical nose to solutions including known substances and identifying the thicknesses of the polymer layers corresponding to these known substances.

Step e) corresponds to "training" the device, as known for electronic noses. In this manner, the reaction of the entire device to a given substance or combination of substance may be determined. The complexity of the device and analyzing techniques involve may be quite variable, depending on the intended use of the device. It is also considered to use such optical noses or the optical sensors themselves for measuring the concentration of a given substance, provided that the device has a measurable response to this characteristic and may be trained accordingly.

Of course, numerous changes may be made to the preferred embodiments described above without departing from the scope of the invention as described in the appended claims.

What is claimed is:

1. An optical nose for identifying at least one substance in a solution, said optical nose comprising:

a plurality of optical sensors, each comprising an optical fiber having a free extremity and a polymer layer deposited on said free extremity, said polymer layer laying in a plane normal to a longitudinal axis of the optical fiber, at least two of said polymer layers being of different types, each polymer layer having a thickness related to said at least one substance when exposed thereto;

a light source, coupled to the optical fiber of each of the optical sensors, for injecting an analytical light beam therein so that said analytical light beam is reflected by the corresponding polymer layer to define a reflected light beam; and a spectrum analyzer coupled to the optical fiber of each of the optical sensors, for receiving each of the reflected light beams, analyzing each of said reflected light beams to deduce therefrom the thickness of the corresponding polymer layer, and identifying the at least one substance corresponding to said thicknesses.

2. An optical nose according to claim 1, wherein the spectrum analyzer comprises a neural network, adapted to identify a plurality of substances based on the corresponding thicknesses of the polymer layers.

3. An optical nose according to claim 1, wherein the analytical light beam includes white light.

4. An optical nose according to claim 1, wherein each optical sensor further comprises:

a source fiber for conveying said analytical light beam from the light source to the optical fiber:

an analyzer fiber for conveying the reflected light beam from the optical fiber to the spectrum analyzer; and a 50/50 coupler for coupling the source fiber and analyzer fiber to the optical fiber.

5. An optical nose according to claim 1, wherein each optical sensor further comprises a reflective optical coating deposited over the polymer layer.

6. An optical nose according to claim 1, wherein each optical sensor further comprises a semi-reflective optical coating extending between the free extremity of the optical fiber and the polymer layer.

7. A method of making an optical nose for identifying at least one substance in a solution, the method comprising the steps of:

a) providing a plurality of optical fibers, each having a free extremity;

b) depositing a polymer layer on the free extremity of each optical fiber in a plane normal to a longitudinal axis of the optical fiber, at least two of said polymer layers being of different types, each polymer layer having a thickness related to the at least one substance when exposed thereto;

c) coupling each of the optical fibers to a light source for injecting an analytical light beam therein, so that said analytical light beam is reflected by the corresponding polymer layer to define a reflected light beam;

d) coupling each of the optical fibers to a spectrum analyzer for receiving each of the reflected light beams, and for analyzing each of said reflected light beams to deduce therefrom the thickness of the corresponding polymer layer; and e) exposing the optical nose to solutions including known substances and identifying the thicknesses of the polymer layers corresponding to said known substances.

* * * * *